United States Patent
Duplat et al.

(10) Patent No.: US 12,396,683 B2
(45) Date of Patent: Aug. 26, 2025

(54) MICROROBOT CONFIGURED TO MOVE IN A VISCOUS MATERIAL

(71) Applicant: ROBEAUTE, Paris (FR)

(72) Inventors: Bertrand Duplat, Paris (FR); Ali Oulmas, Paris (FR); Quentin Francois, Paris (FR)

(73) Assignee: ROBEAUTE, Paris (FR)

( * ) Notice: Subject to any disclaimer, the term of this patent is extended or adjusted under 35 U.S.C. 154(b) by 1003 days.

(21) Appl. No.: 17/599,096

(22) PCT Filed: Mar. 27, 2020

(86) PCT No.: PCT/EP2020/058755
§ 371 (c)(1),
(2) Date: Sep. 28, 2021

(87) PCT Pub. No.: WO2020/201108
PCT Pub. Date: Oct. 8, 2020

(65) Prior Publication Data
US 2022/0160304 A1    May 26, 2022

Related U.S. Application Data

(63) Continuation of application No. 16/369,508, filed on Mar. 29, 2019, now abandoned.

(51) Int. Cl.
*A61B 5/00*       (2006.01)
*A61B 17/00*     (2006.01)
(Continued)

(52) U.S. Cl.
CPC .......... *A61B 5/6847* (2013.01); *A61B 34/72* (2016.02); *A61B 2017/00318* (2013.01);
(Continued)

(58) Field of Classification Search
CPC ........... A61B 2017/00318; A61B 2017/00345; A61B 34/32
(Continued)

(56) References Cited

U.S. PATENT DOCUMENTS

| | | | |
|---|---|---|---|
| 4,389,208 | A | 6/1983 | LeVeen et al. |
| 5,662,587 | A | 9/1997 | Grundfest et al. |
| 2010/0145143 | A1 | 6/2010 | Salomon et al. |

FOREIGN PATENT DOCUMENTS

| | | | |
|---|---|---|---|
| CN | 101743157 A | | 6/2010 |
| CN | 102734594 A | * | 10/2012 |

(Continued)

OTHER PUBLICATIONS

Translation CN-102734594-A (Year: 2024).*
(Continued)

*Primary Examiner* — J. Todd Newton
(74) *Attorney, Agent, or Firm* — Maier & Maier, PLC

(57) ABSTRACT

A microrobot configured to move in a viscous material, in particular in an organ of a subject such as a brain, the microrobot having a propulsion structure comprising a head portion, a rear portion and a deformable portion connecting the head portion and the rear portion. The deformable portion is deformable in elongation/contraction along a main axis connecting the head portion and the rear portion. The head portion includes at its surface at least one propulsion cilium, one end of the at least one propulsion cilium being attached to the head portion and the other end of the at least one propulsion cilium being a free end configured to move freely in the viscous material. The propulsion structure further includes a motor configured to actuate sequentially elongation/contraction cycles of the deformable portion.

13 Claims, 6 Drawing Sheets

(51) Int. Cl.
    *A61B 34/00*     (2016.01)
    *A61B 34/30*     (2016.01)
    *B25J 7/00*     (2006.01)

(52) U.S. Cl.
    CPC ..... *A61B 2017/00345* (2013.01); *A61B 34/30* (2016.02); *A61B 2034/301* (2016.02); *A61B 2034/302* (2016.02); *A61B 2034/303* (2016.02); *A61B 2560/02* (2013.01); *A61B 2560/04* (2013.01); *B25J 7/00* (2013.01)

(58) Field of Classification Search
    USPC .................................................. 267/221, 275
    See application file for complete search history.

(56) References Cited

FOREIGN PATENT DOCUMENTS

| | | | |
|---|---|---|---|
| CN | 205806301 U | * | 12/2016 |
| CN | 107934912 A | * | 4/2018 |
| FR | 3056391 A1 | | 3/2018 |
| JP | 2002127100 A | | 5/2002 |
| JP | 2004073887 A | | 3/2004 |
| JP | 2007259666 A | | 10/2007 |
| WO | 2018/154326 A1 | | 8/2018 |

OTHER PUBLICATIONS

Translation CN-107934912-A (Year: 2024).*
Translation CN-205806301-U (Year: 2024).*
International Search Report issued on Jul. 1, 2020 in corresponding International application No. PCT/EP2020/058755; 3 pages.
Kim et al., "An earthworm-like micro robot using shape memory alloy actuator", Sensors and Actuators A, 2006, pp. 429-437, vol. 125; 9 pages.
Nemitz et al., "Using Voice Coils to Actuate Modular Soft Robots: Wormbot, an Example", Soft Robotics, 2016, pp. 198-204, vol. 3; 7 pages.
Palagi et al., "Structured light enables biomimetic swimming and versatile locomotion of photoresponsive soft microrobots", Nature Materials, 2016, pp. 647-653, vol. 15; 8 pages.

* cited by examiner

MICROROBOT CONFIGURED TO MOVE IN A VISCOUS MATERIAL

FIELD

The present invention relates to a microrobot configured to move in a viscous material, in particular in an organ of a subject such as a brain. Such a microrobot may be used to perform various biomedical operations, such as minimally invasive surgery, accurately targeted therapy, etc.

BACKGROUND

The ability to reach deep and functional structures without damage is a major challenge in mini-invasive surgery, especially in neurosurgery. Thanks to microtechnologies, it becomes possible to send a fully autonomous microrobot inside an organ of a subject, such as a brain. However, the propulsion of a microrobot in an environment at low Reynolds number, as is the brain, is a challenge because of absence of inertia and presence of relatively high drag forces due to the small size of the microrobot. Another important requirement is that the microrobot should be capable of moving in an organ while limiting as much as possible the physiological damage that its passage causes to the organ.

In this context, the invention is intended to propose a microrobot having a highly efficient propulsion mechanism in a fluid environment at low Reynolds number, while preserving as much as possible the integrity of the environment in which it is displaced.

SUMMARY

For this purpose, a subject of the invention is a microrobot configured to move in a viscous material, in particular in an organ of a subject such as a brain, the microrobot having a propulsion structure comprising a head portion, a rear portion and a deformable portion connecting the head portion and the rear portion, the deformable portion being deformable in elongation/contraction along a main axis connecting the head portion and the rear portion, wherein the head portion comprises at its surface at least one propulsion cilium, one end of the at least one propulsion cilium being attached to the head portion and the other end of the at least one propulsion cilium being a free end configured to move freely in the viscous material, wherein the propulsion structure further comprises an actuator configured to actuate sequentially elongation/contraction cycles of the deformable portion.

Thanks to the specific structure of the microrobot according to the invention, a longitudinal propulsion movement of the microrobot is obtained, similarly to a swimming cycle for a swimmer. In particular, the sequential elongation/contraction cycles of the deformable portion, which are controlled by way of the actuator, cause a displacement of the propulsion cilia in the viscous material, thus inducing a net propulsive force due to the interaction of the propulsion cilia with the viscous material.

Within the frame of the invention, a microrobot is a robot of outer diameter less than five millimeters, in particular of the order of 1 to 2 millimeters or less.

According to one embodiment, for each elongation/contraction cycle of the deformable portion actuated by the actuator, the path of the free end of the at least one propulsion cilium in the viscous material in the contraction phase of the deformable portion is different from the path of the free end of the at least one propulsion cilium in the viscous material in the elongation phase of the deformable portion. Such an implementation of the propulsion cilia relative to the elongation and contraction phases of the deformable portion makes it possible to obtain a non-reciprocal motion of the microrobot, which enables effective locomotion within fluidic materials at low Reynolds number. In particular, in non-limitative illustrative embodiments, the path of the free end of the at least one propulsion cilium in the viscous material is topologically equivalent to an elliptical path or a circular path for each elongation/contraction cycle of the deformable portion. It is noted that a path of the free end topologically equivalent to a line segment is not appropriate to obtain a non-reciprocal motion of the microrobot, even if different dynamics are applied along the path.

According to one embodiment, the at least one propulsion cilium comprises a cilium body having an asymmetric cross section taken transversely to a longitudinal axis of the cilium body. Such an asymmetric structure of the at least one propulsion cilium contributes to achieving a non-reciprocal motion of the microrobot. More precisely, due to the asymmetric cross section of the cilium body, each propulsion cilium is deformed non-symmetrically under the effect of the viscous material, in each elongation/contraction cycle of the deformable portion, such that the propulsion cilium may be bent or twisted.

According to one embodiment, the at least one propulsion cilium comprises a cilium body and an enlarged end portion forming the free end of the at least one propulsion cilium, the cross-sectional area of the enlarged end portion taken transversely to a longitudinal axis of the cilium body being less than the cross-sectional area of the enlarged end portion in at least one plane parallel to the longitudinal axis of the cilium body. In one embodiment, the cross-sectional area of the enlarged end portion taken transversely to a longitudinal axis of the cilium body is substantially equal to or less than the cross-sectional area of the cilium body, whereas the cross-sectional area of the enlarged end portion in at least one plane parallel to the longitudinal axis of the cilium body is higher than the cross-sectional area of the cilium body. Such an enlarged end portion of the at least one propulsion cilium also contributes to obtaining a non-reciprocal motion of the microrobot. In particular, once the propulsion cilium is deformed, for example bent or twisted, the higher cross-sectional area of the enlarged end portion, which was initially oriented parallel to the displacement, becomes oriented transversally to the displacement, such that the forces exerted by the viscous material are exerted on a higher cross-sectional area. Then, the resistance of the propulsion cilium is higher, and the path of the free end of the propulsion cilium in the viscous material is changed.

According to one embodiment, the rear portion comprises at its surface at least one propulsion cilium. Within the frame of the invention, it is understood that the presence of propulsion cilia only on the head portion is sufficient. Yet, an arrangement with propulsion cilia provided also on the rear portion may contribute to the propulsion of the microrobot in the viscous material.

According to one embodiment, when the rear portion comprises at its surface at least one propulsion cilium, the at least one propulsion cilium of the rear portion may be identical or different from the at least one propulsion cilium of the head portion.

According to one embodiment, the front portion comprises a plurality of propulsion cilia arranged on the front portion in a helical configuration so as to cause a rotational movement of the microrobot about the main axis when it moves forward. Such an implementation makes it possible to obtain, in addition to the longitudinal propulsion movement, a rotational movement of the microrobot about the main axis, with the effect of improving the penetration of the microrobot into the viscous material. When the rear portion comprises propulsion cilia, the propulsion cilia may also be arranged on the rear portion in a helical configuration so as to cause a rotational movement of the microrobot about the main axis when it moves forward.

According to one embodiment, the deformable portion comprises a bellows member having a front end attached to the head portion and a rear end attached to the rear portion. In one embodiment, the ratio of the thickness of the peak and valley portions of the peripheral wall of the bellows member to the thickness of the junction portions between two successive peak and valley portions of the peripheral wall of the bellows member is higher than 2, preferably higher than 5, more preferably higher than 10. Thanks to this thickness variation, the thinner junction portions can bear against the thicker peak and valley portions in each elongation/contraction cycle, which enhances the stability and the efficiency of the deformation of the deformable portion.

According to one embodiment, the deformable portion comprises a spring member having a front end attached to the head portion and a rear end attached to the rear portion. In one embodiment, the spring member comprises one leg arranged helically. In another embodiment, the spring member comprises at least three legs arranged helically relative to one another.

According to one embodiment, the deformable portion comprises a combination of a bellows member and a spring member, each valley portion of the bellows member being positioned between two successive turns of the spring member.

According to one embodiment, the deformable portion is made of a material having a Young's modulus between 0.001 and 10 GPa, preferably between 0.1 and 10 GPa, even more preferably between 0.5 and 2 GPa. In one embodiment, all of the head portion, the rear portion and the deformable portion are made of the same material. In one embodiment, the material of the head portion, the rear portion and the deformable portion is a biocompatible polymer. An example of a material that may be used for the head portion, the rear portion and/or the deformable portion is a UV-curable hybrid inorganic-organic polymer such as ORMOCLEAR manufactured by the company MICRO RESIST TECHNOLOGY GmbH.

According to one embodiment, the at least one propulsion cilium of the head portion and/or the rear portion is made of a material having a Young's modulus between 0.001 and 10 GPa, preferably between 0.1 and 10 GPa, even more preferably between 0.5 and 2 GPa. According to one embodiment, the at least one propulsion cilium is made of the same material as the deformable portion. In one embodiment, the material of the at least one propulsion cilium is a biocompatible polymer. Examples of materials that may be used for the at least one propulsion cilium include polydimethylsiloxane (PDMS), silicon, or a UV-curable hybrid inorganic-organic polymer such as ORMOCLEAR.

According to one embodiment, the microrobot comprises at least two propulsion structures positioned in a row, in particular end to end, wherein the actuators of the propulsion structures are configured to actuate elongation/contraction cycles of the deformable portions of the propulsion structures in predefined sequences so as to generate a non-reciprocal motion of the microrobot in the viscous material. Such an arrangement is another way to obtain a non-reciprocal motion of the microrobot, enabling effective locomotion within fluids at low Reynolds number. This arrangement may be used alone, or in combination with the configurations of the at least one propulsion cilium for generating a non-reciprocal motion as described above.

According to one embodiment, the actuator comprises a piezoelectric transducer.

According to one embodiment, the actuator comprises a pump, in particular an electroosmotic pump. This embodiment is suitable when the deformable portion can contain a fluid in its interior volume, in particular when the deformable portion has a continuous peripheral wall. In one embodiment, the deformable portion comprises a bellows member and the actuator comprises a pump, in particular an electroosmotic pump.

According to one embodiment, the actuator comprises an electromagnetic transducer including a combination of an electromagnetic coil attached at one end of the deformable portion and a permanent magnet attached at the other end of the deformable portion.

According to one embodiment, the actuator comprises a photoreactive material included in the deformable portion, where the photoreactive material is configured to retract or extend under the effect of light, and a luminous source provided in the vicinity of the deformable portion, in particular by a fiber optic, so that the photoreactive material can receive light from the luminous source. An example of a suitable photoreactive actuator comprises a dual-photoresponsive liquid crystalline-based actuator, in particular containing an azomerocyanine dye locally converted into the hydroxyazopyridinium form by acid treatment.

According to one embodiment, the microrobot is configured to move in a fluidic material at low Reynolds number, with a Reynolds number Re between $10^{-7}$ and $10^{-1}$ and preferably between $10^{-5}$ and $10^{-1}$. In a known manner, the Reynolds number Re is a dimensionless quantity quantifying the relative importance of inertial forces and viscous forces for given flow conditions. It can be expressed as the ratio of inertial forces to viscous forces in a fluid: $Re=uL/v$, where u is the mean velocity of the fluid with respect to the object, L is a characteristic linear dimension, v is the kinematic viscosity of the fluid.

BRIEF DESCRIPTION OF THE DRAWINGS

Features and advantages of the invention will become apparent from the following description of several embodiments of a microrobot according to the invention, this description being given merely by way of example and with reference to the appended drawings in which.

DETAILED DESCRIPTION

Figure 1:
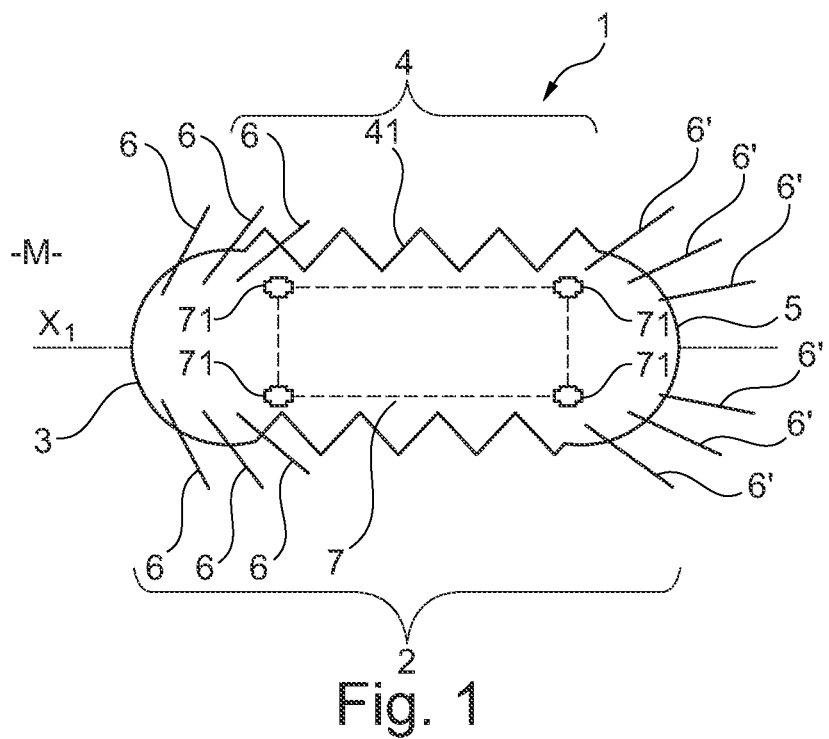
FIG. 1 is a schematic cross section of a microrobot according to a first embodiment of the invention, comprising a deformable portion in the form of a bellows member and a piezoelectric actuator.

FIG. 1 is a schematic cross section of a microrobot 1 according to a first embodiment of the invention. The microrobot 1 is configured to move in a viscous material M, such as the cerebrospinal fluid or the extracellular matrix of the brain of a subject which are low Reynolds number fluidic materials for the microrobot 1. To this end, the microrobot 1 has a propulsion structure 2 comprising a head portion 3, a rear portion 5 and a deformable portion 4 connecting the head portion 3 and the rear portion 5. In the first embodiment shown in FIG. 1, the deformable portion 4 is a bellows member 41 deformable in elongation/contraction along a main axis $X_1$ of the microrobot 1 connecting the head portion 3 and the rear portion 5. The propulsion structure 2 further comprises a piezoelectric actuator 7 configured to actuate sequentially elongation/contraction cycles of the bellows member 41.

As visible in FIG. 1, the head portion 3 comprises at its surface a plurality of propulsion cilia 6, configured to interact with the viscous material M. In this first embodiment, the rear portion 5 also comprises at its surface a plurality of propulsion cilia 6' that are identical to the propulsion cilia 6 of the head portion 3. The sequential elongation/contraction cycles of the bellows member 41 actuated by the piezoelectric actuator 7 cause a displacement of the propulsion cilia 6, 6' in the viscous material M, thus producing a propulsive force, which results in a movement of the microrobot 1. In the example shown schematically in FIG. 1, the piezoelectric actuator 7 is housed inside the bellows member 41, with support points 71 on the bellows member 41 so as to transmit elongation/contraction movements along the main axis $X_1$ from the actuator 7 to the bellows member 41. As a variant, the piezoelectric actuator 7 may be attached at the rear end to the bellows member 41, e.g. fixed to the rear portion 5.

Figure 14:
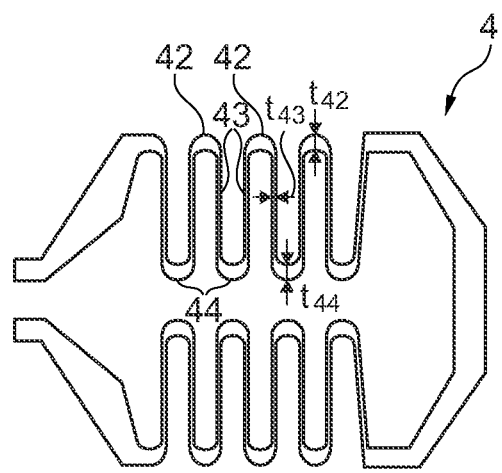
FIG. 14 is a schematic cross section of a bellows member of a microrobot according to the invention.

As shown in FIG. 14, the bellows member 41 advantageously has a variable thickness, such that the peak portions 42 and the valley portions 44 of the peripheral wall of the bellows member 41 have a higher thickness than the junction portions 43 between the successive peak and valley portions. Advantageously, the ratio of the thickness $t_{42}$, $t_{44}$ of the peak portions 42 and the valley portions 44 to the thickness $t_{43}$ of the junction portions 43 is higher than 2, preferably higher than 5, more preferably higher than 10. Thanks to this thickness variation, the thinner junction portions 43 can bear against the thicker peak portions 42 and valley portions 44 in each elongation/contraction cycle, which enhances the stability and efficiency of the deformation of the bellows member 41.

Figure 13:
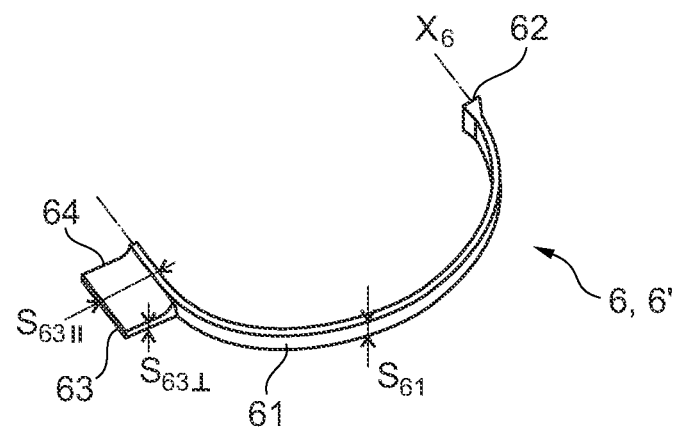
FIG. 13 is a perspective view of a propulsion cilium of a microrobot according to the invention.

As shown in FIG. 13, each propulsion cilium 6, 6' has one end 62 attached to the head portion 3 or rear portion 5, whereas the other end 64 of the propulsion cilium 6, 6' is a free end configured to move freely in the viscous material M. In the embodiment shown in FIG. 13, each propulsion cilium 6, 6' comprises a cilium body 61 and an enlarged end portion 63 forming the free end 64 of the propulsion cilium. The cilium body 61 has an asymmetric cross section taken transversely to a longitudinal axis $X_6$ of the cilium body, e.g. a cross section having a triangular shape. In addition, the cross-sectional area $S_{63\perp}$ of the enlarged end portion 63 taken transversely to the longitudinal axis $X_6$ of the cilium body 61 is substantially equal to or less than the cross-sectional area $S_{61}$ of the cilium body 61, whereas the cross-sectional area $S_{63//}$ of the enlarged end portion 63 in at least one plane parallel to the longitudinal axis $X_6$ of the cilium body 61 is higher than the cross-sectional area $S_{61}$ of the cilium body.

Due to the asymmetric cross section of the cilium body 61, each propulsion cilium 6, 6' is deformed non-symineirically under the effect of the viscous material M in each elongation/contraction cycle of the bellows member 41. Thus, the propulsion cilium 6, 6' is bent under the effect of the viscous material M. Once the propulsion cilium 6, 6' is bent, the higher cross-sectional area $S_{63//}$ of the enlarged end portion 63, which was initially oriented parallel to the displacement, becomes oriented transversally to the displacement, such that the forces exerted by the viscous material M are exerted on a higher cross-sectional area. Then, the resistance of the propulsion cilium 6, 6' against the viscous material M is higher, and the path of the free end 64 of the propulsion cilium 6, 6' in the viscous material M is changed.

With this specific structure of the propulsion cilium 6, 6' as shown in FIG. 13, for each elongation/contraction cycle of the bellows member 41 actuated by the piezoelectric actuator 7, the path of the free end 64 of the propulsion cilium in the viscous material M in the contraction phase of the bellows member 41 is different from the path of the free end 64 in the viscous material M in the elongation phase of the bellows member 41. It has been observed that the path of the free end 64 of the propulsion cilium 6, 6' in the viscous material M is topologically equivalent to an elliptical path or a circular path for each elongation/contraction cycle. A non-reciprocal motion of the microrobot 1 is thus obtained, enabling effective locomotion of the microrobot 1 within fluidic materials at low Reynolds number, such as the cerebrospinal fluid or the extracellular matrix of the brain.

Optionally, the propulsion cilia 6, 6' may be arranged on the front portion 3 and on the rear portion 5 in a helical configuration so as to cause a rotational movement of the microrobot 1 about the main axis $X_1$ when it moves forward. In the same way as a corkscrew, a rotational movement of the microrobot 1 about the main axis $X_1$ is thus obtained, in addition to the longitudinal propulsion movement, which improves the penetration of the microrobot 1 into the viscous material M.

Figure 2:
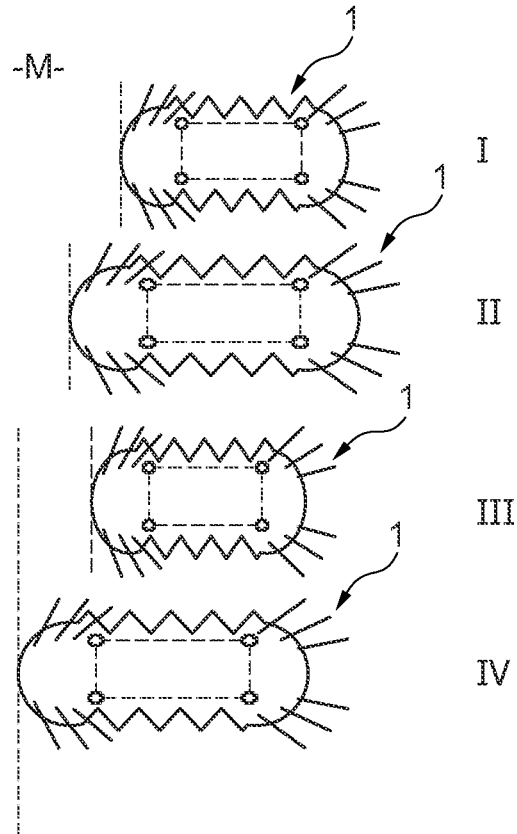
FIG. 2 is a view of four successive configurations (I-IV) of the microrobot of FIG. 1 in a forward movement in a viscous material.

FIG. 2 shows four successive configurations I, II, III, IV of the microrobot 1 of FIG. 1 in a forward movement in the viscous material M according to elongation/contraction cycles of the bellows member 41. In the configuration I, the bellows member 41 is in a contracted state. In the configuration II, the piezoelectric actuator 7 is in an elongation position, thus elongating the bellows member 41. In this configuration, the propulsion cilia 6, 6' bear against the viscous material M and propel the microrobot 1 forward. In the configuration III, the bellows member 41 is again in a contracted state, which may generate a very slight rear movement of the microrobot 1. Then, in the configuration IV, the microrobot 1 again moves forward with a much greater forward movement than the rear movement in the configuration III.

As a non-limiting example, a microrobot 1 according to the invention having the following characteristics has proven propulsion performance in fluidic materials at low Reynolds number:
- The total length of the microrobot was 3 mm and the diameter of the microrobot was 900 µm;
- The bellows member 41 had a length of 600 µm; the thickness $t_{42}$, $t_{44}$ of the peak portions 42 and the valley portions 44 was 30 µm; the thickness $t_{43}$ of the junction portions 43 was 3 µm;
- For each propulsion cilium 6, 6', the cross-sectional area $S_{61}$ of the cilium body 61 was 2500 µm$^2$; the transverse cross-sectional area $S_{63}\perp$ of the enlarged end portion 63 was 2500 µm$^2$; the parallel cross-sectional area $S_{63//}$ of the enlarged end portion 63 was 15000 µm$^2$;

The head portion 3, the rear portion 5 and the bellows member 41 were formed as a one-piece unit, fabricated by 3D laser lithography using UV-curable hybrid inorganic-organic polymer ORMOCLEAR as a photoresist. The photoresist was applied on a glass substrate and a laser spot selectively polymerized the photoresist according to a 3D CAD design. In this particular example, the propulsion cilia 6, 6' were manufactured integrally with the head portion 3 and the rear portion 5, i.e. they were made of the same material as the head portion 3 and the rear portion 5.

Figure 3:
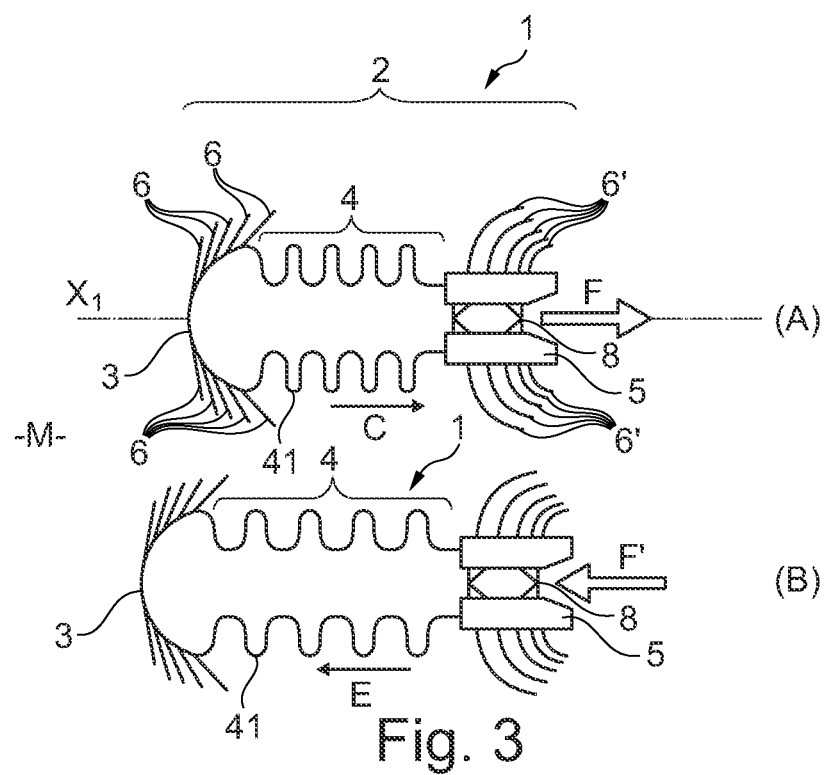
FIG. 3 is a schematic cross section of a microrobot according to a second embodiment of the invention, comprising a deformable portion in the form of a bellows member and an actuator in the form of a pump connected to the bellows member and open at the rear side, showing two successive configurations of the microrobot in a forward movement in a viscous material including a contraction phase (A) and an elongation phase (B)

In the second embodiment shown in FIG. 3, elements similar to those of the first embodiment bear identical references. The microrobot 1 of the second embodiment differs from the first embodiment in that the actuator is in the form of a pump 8 connected to the bellows member 41 and open at the rear side. By way of a non-limiting example, the pump 8 may be an electroosmotic pump. In this second embodiment, the viscous material M is pumped in and out of the bellows member 41 by the pump 8. As shown by the arrow F of FIG. 3(A), in the contraction phase the viscous material M is ejected out of the bellows member 41 by the pump 8 and the bellows member 41 is contracted. In the elongation phase shown in FIG. 3(B), the viscous material M is pumped into the interior volume of the bellows member 41 by the pump 8, as shown by the arrow F', which elongates the bellows member 41. The propulsion cilia 6, 6' bear against the viscous material M and propel the microrobot 1 forward.

Figure 4:
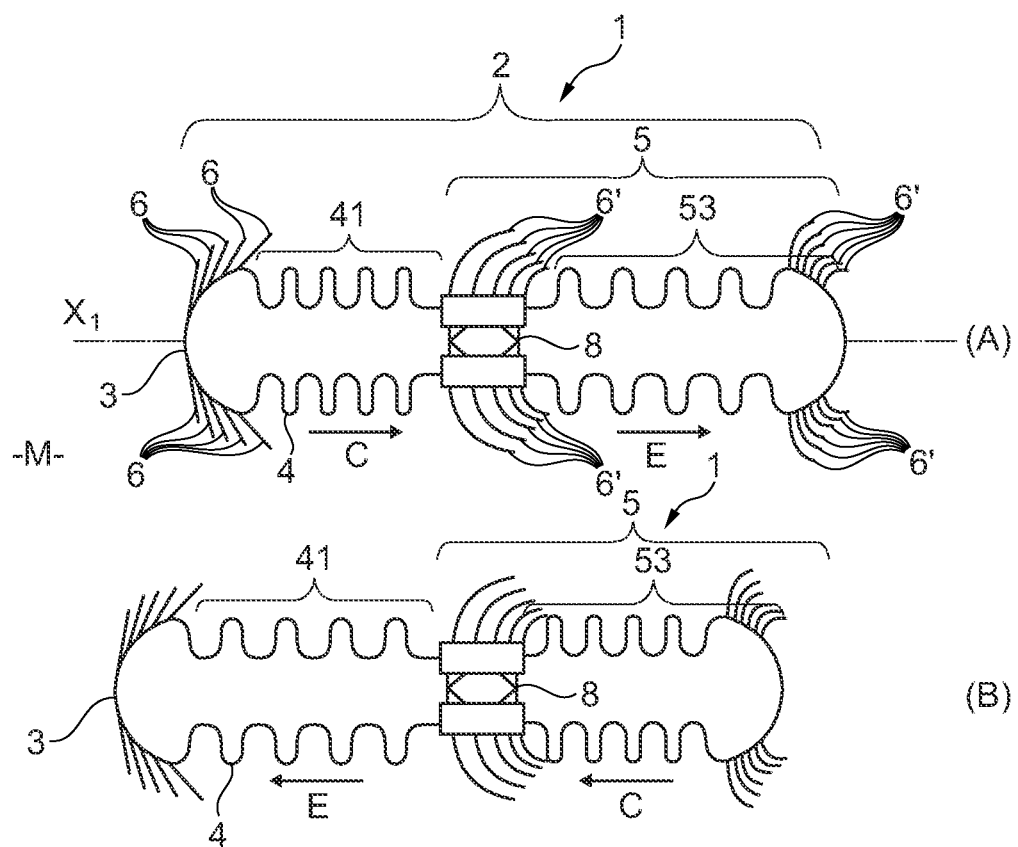
FIG. 4 is a schematic cross section of a microrobot according to a third embodiment of the invention, comprising a deformable portion in the form of a front bellows member and an actuator in the form of a pump connected between the front bellows member and a rear bellows member, showing two successive configurations of the microrobot in a forward movement in a viscous material including a contraction phase (A) and an elongation phase (B)

In the third embodiment shown in FIG. 4, elements similar to those of the second embodiment bear identical references. The microrobot 1 of the third embodiment differs from the second embodiment in that the pump 8 is connected between a front bellows member 41 at one end and a rear bellows member 53 at the other end, where the front bellows member 41 is the deformable portion 4 whose elongation/contraction cycles are used to propel the microrobot, whereas the rear bellows member 53 is part of the rear portion 5. Compared to the second embodiment, this arrangement has the advantage that the viscous material M is not pumped in and out of the deformable portion 4, which limits the impact on the viscous material M. Instead, the pump 8 uses a fluid internal to the microrobot 1, which may be water for example, to generate the elongation/contraction cycles of the front bellows member 41. In the contraction phase shown in FIG. 4(A), the pumped fluid is ejected out of the front bellows member 41 and injected into the interior volume of the rear bellows member 53 by the pump 8, so that the front bellows member 41 is contracted. In the elongation phase shown in FIG. 4(B), the pumped fluid is ejected out of the rear bellows member 53 and injected into the interior volume of the front bellows member 41 by the pump 8, which elongates the front bellows member 41. As mentioned previously, the propulsion cilia 6, 6' bear against the viscous material M and propel the microrobot 1 forward.

Figure 5:
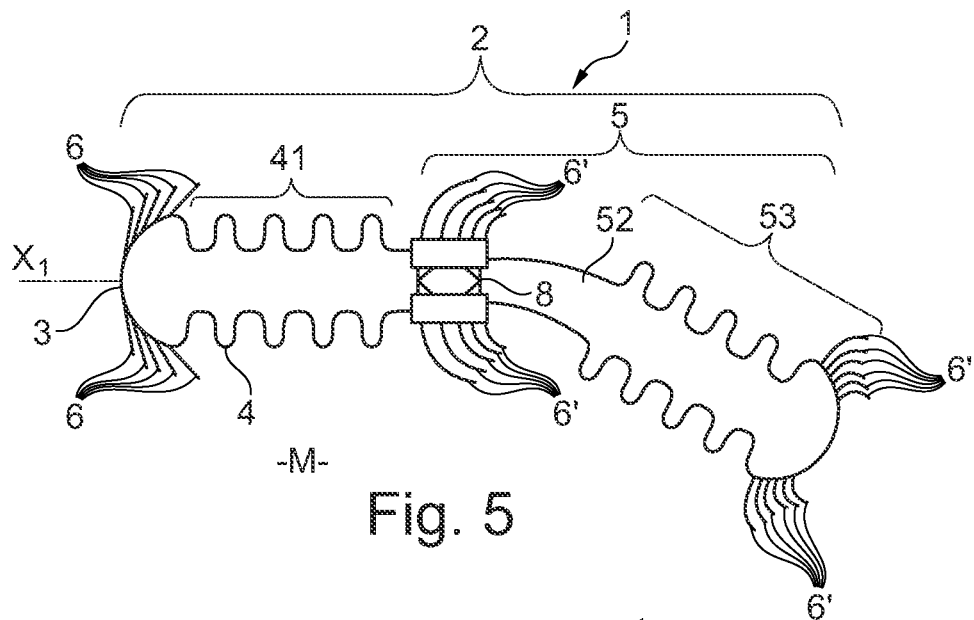
FIG. 5 is a schematic cross section of a microrobot according to a fourth embodiment of the invention, comprising a deformable portion in the form of a front bellows member an actuator in the form of a pump connected between the front bellows member and a rear bellows member using a flexible tube.

In the fourth embodiment shown in FIG. 5, elements similar to those of the third embodiment bear identical references. The microrobot 1 of the fourth embodiment differs from the third embodiment in that the pump 8 is connected between the front bellows member 41 and the rear bellows member 53 using a flexible tube 52, so that the rear portion 5 may rotate relative to the front bellows member 41 and the front portion 3, instead of remaining aligned therewith.

Figure 6:
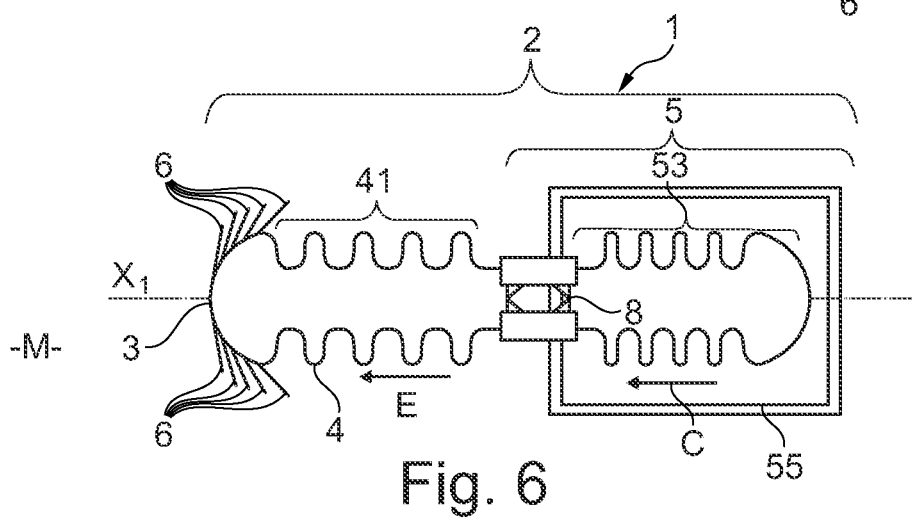
FIG. 6 is a schematic cross section of a microrobot according to a fifth embodiment of the invention, comprising a deformable portion in the form of a front bellows member and an actuator in the form of a pump connected between the front bellows member and a rear bellows member, the rear bellows member being housed in a rigid casing.

In the fifth embodiment shown in FIG. 6, elements similar to those of the third embodiment bear identical references. The microrobot 1 of the fifth embodiment differs from the third embodiment in that the rear bellows 53 member is housed in a rigid casing 55. In this way, the elongation/contraction cycles of the rear bellows 53 do not interfere with the desired forward movement of the microrobot 1.

Figure 7:
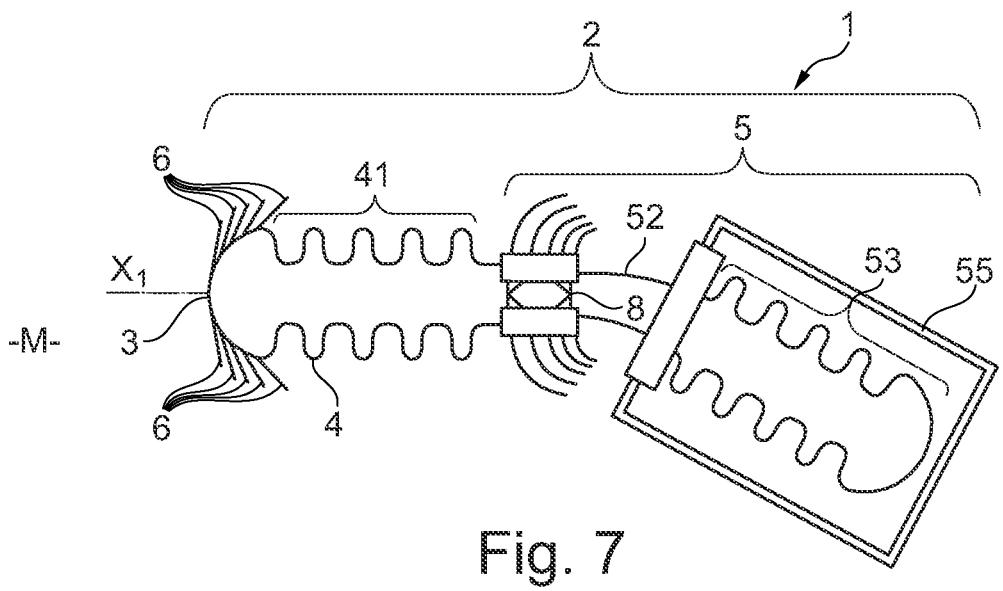
FIG. 7 is a schematic cross section of a microrobot according to a sixth embodiment of the invention, comprising a deformable portion in the form of a front bellows member and an actuator in the form of a pump connected between the front bellows member and a rear bellows member using a flexible tube, the rear bellows member being housed in a rigid casing.

In the sixth embodiment shown in FIG. 7, elements similar to those of the fifth embodiment bear identical references. The microrobot 1 of the sixth embodiment differs from the fifth embodiment in that the pump 8 is connected using a flexible tube 52 between the front bellows member 41 and the rear bellows member 53 housed in a rigid casing 55. As explained previously with reference to the fourth embodiment of FIG. 5, with such a flexible tube 52, the rear portion 5 may rotate relative to the front bellows member 41 and the front portion 3, instead of remaining aligned therewith.

Figure 8:
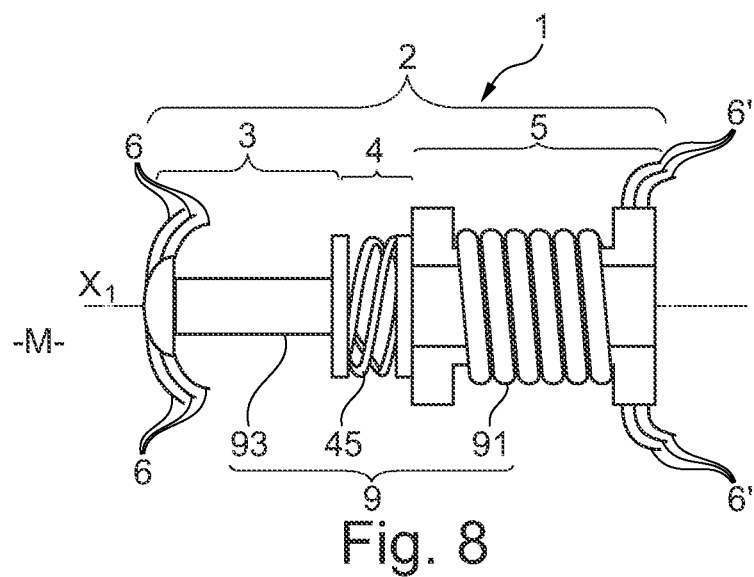
FIG. 8 is a schematic cross section of a microrobot according to a seventh embodiment of the invention, comprising a deformable portion in the form of a spring member and an electromagnetic actuator, the permanent magnet of the electromagnetic actuator being positioned outside the spring member.

In the seventh embodiment shown in FIG. 8, elements similar to those of the first embodiment bear identical references. The microrobot 1 of the seventh embodiment differs from the first embodiment in that the deformable portion is in the form of a spring member 45 and the actuator is an electromagnetic actuator 9 comprising an electromagnetic coil 91 and a permanent magnet 93 positioned outside the spring member 45. More precisely, the permanent magnet 93 is part of the front portion 3 and attached to the front end of the spring member 45, whereas the electromagnetic coil 91 is part of the rear portion 5 and attached to the rear end of the spring member 45. Depending on the current applied to the electromagnetic coil 91, the permanent magnet 93 moves toward or away from the electromagnetic coil 91, which in turn produces a contraction or elongation of the spring member 45. As mentioned previously, the propulsion cilia 6, 6' bear against the viscous material M and propel the microrobot 1 forward.

Figure 9:
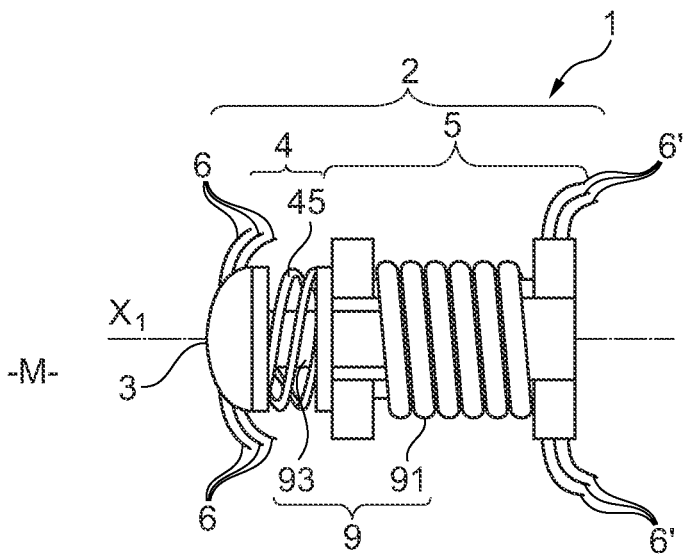
FIG. 9 is a schematic cross section of a microrobot according to an eighth embodiment of the invention, comprising a deformable portion in the form of a spring member and an electromagnetic actuator, the permanent magnet of the electromagnetic actuator being housed inside the spring member.

In the eighth embodiment shown in FIG. 9, elements similar to those of the seventh embodiment bear identical references. The microrobot 1 of the eighth embodiment differs from the seventh embodiment in that the permanent magnet 93 of the electromagnetic actuator 9 is housed inside the spring member 45. Thanks to this arrangement, the design of the microrobot 1 is more compact.

Figure 10:
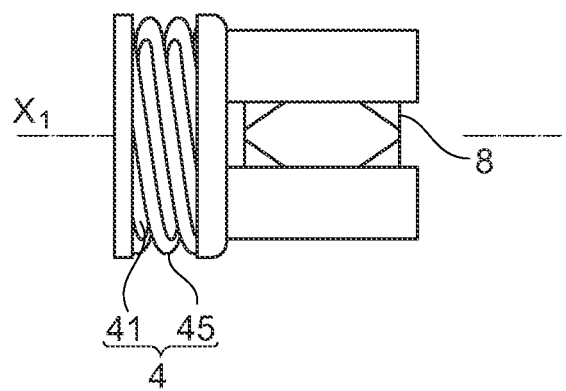
FIG. 10 is a partial view of a microrobot according to a ninth embodiment of the invention, comprising a deformable portion formed by a combination of a bellows member and a spring member, and an actuator in the form of a pump.

In the ninth embodiment shown in FIG. 10, elements similar to those of the first embodiment bear identical references. The microrobot 1 of the ninth embodiment differs from the previous embodiments involving a pump 8 (i.e. the embodiments of FIGS. 3 to 7) in that the deformable portion 4 is formed by a combination of a bellows member 41 and a spring member 45, where each valley portion 44 of the bellows member 41 is positioned between two successive turns of the spring member 45.

Figure 11:
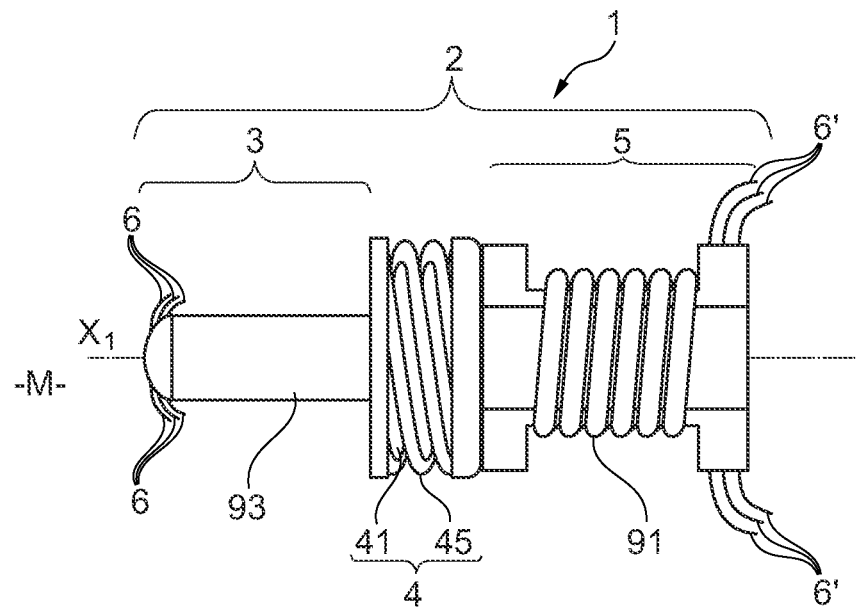
FIG. 11 is a schematic cross section of a microrobot according to a tenth embodiment of the invention, comprising a deformable portion formed by a combination of a bellows member and a spring member, and an electromagnetic actuator where the permanent magnet of the electromagnetic actuator is positioned outside the deformable portion.

In the tenth embodiment shown in FIG. 11, elements similar to those of the seventh embodiment bear identical references. The microrobot 1 of the tenth embodiment differs from the seventh embodiment in that the deformable portion 4 is formed by a combination of a bellows member 41 and a spring member 45, the permanent magnet 93 of the electromagnetic actuator 9 being positioned outside the deformable portion 4.

Figure 12:
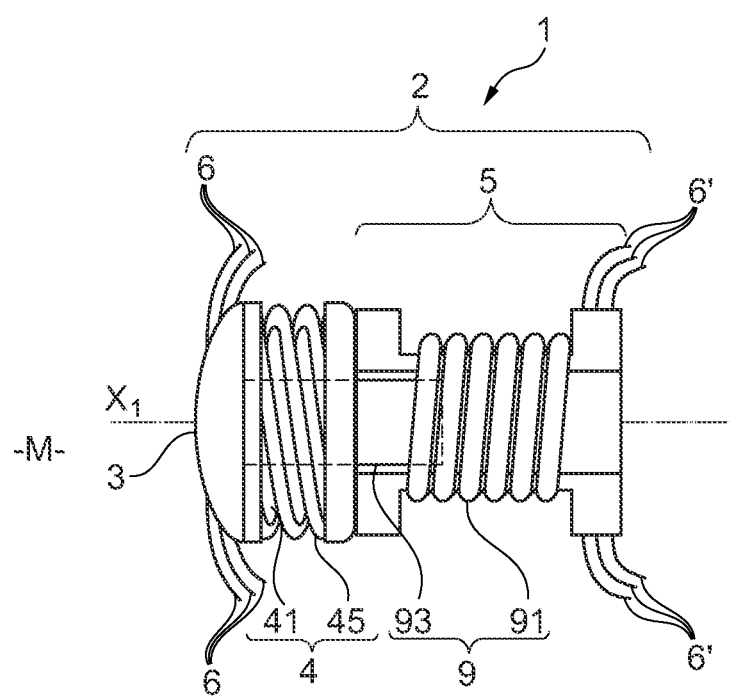
FIG. 12 is a schematic cross section of a microrobot according to an eleventh embodiment of the invention, comprising a deformable portion formed by a combination of a bellows member and a spring member, and an electromagnetic actuator where the permanent magnet of the electromagnetic actuator is housed inside the deformable portion.

In the eleventh embodiment shown in FIG. 12, elements similar to those of the eighth embodiment bear identical references. The microrobot 1 of the eleventh embodiment differs from the eighth embodiment in that the deformable portion 4 is formed by a combination of a bellows member 41 and a spring member 45, the permanent magnet 93 of the electromagnetic actuator 9 being housed inside the deformable portion 4.

Figure 15:
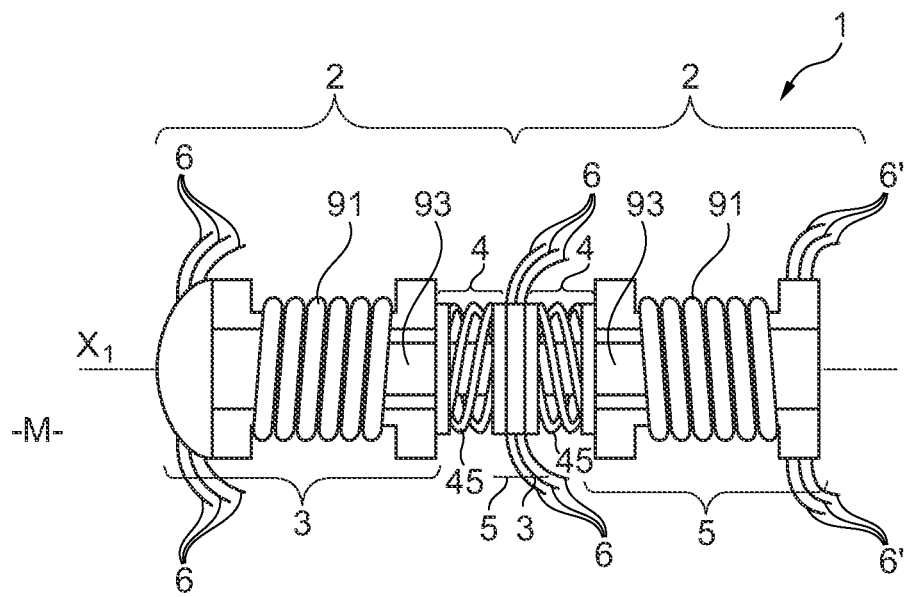
FIG. 15 is a schematic cross section of a microrobot according to a twelfth embodiment of the invention, comprising two propulsion structures positioned end to end.

In the twelfth embodiment shown in FIG. 15, elements similar to those of the eighth embodiment bear identical references. The microrobot 1 of the twelfth embodiment differs from the eighth embodiment in that the microrobot 1 comprises two propulsion structures 2 positioned end to end. In this embodiment, the electromagnetic actuators of the two propulsion structures 2 are advantageously configured to actuate elongation/contraction cycles of the two deformable portions 4 in predefined sequences so as to generate a non-reciprocal motion of the microrobot 1 in the viscous material M. Such an arrangement makes it possible to obtain a non-reciprocal motion of the microrobot 1 in addition to the specific structure of the propulsion cilia 6, 6', which further improves the propulsion efficiency of the microrobot 1 within the viscous material M.

The invention is not limited to the examples described and shown. In particular, any combination of the types and arrangements of the deformable portions and actuators described above can be considered for a microrobot according to the invention, even when not been explicitly described or shown in the figures. For example, a microrobot according to the invention can include a bellows member (without a spring member) associated to an electromagnetic actuator, even if this combination has not been explicitly described or illustrated.

In addition, other types and arrangements of the deformable portions and actuators described above can be considered for a microrobot according to the invention. For example, the actuator of a microrobot according to the invention can be a photoresponsive actuator, e.g. comprising a photoreactive material included in the deformable portion, where the photoreactive material is configured to retract or extend under the effect of light, and a luminous source provided in the vicinity of the deformable portion, in particular by a fiber optic, so that the photoreactive material can receive light from the luminous source.

Moreover, the arrangement with at least two propulsion structures positioned in a row and actuation of the elongation/contraction cycles in predefined sequences so as to generate a non-reciprocal motion of the microrobot, as shown in the embodiment of FIG. 15, has been described in combination with the presence of propulsion cilia also generating a non-reciprocal motion. However, for a microrobot according to the invention, the arrangement with at least two propulsion structures so as to generate a non-reciprocal motion can be used alone, without the presence of propulsion cilia as described above.

The invention claimed is:

1. A microrobot configured to move in a viscous material, the microrobot having a propulsion structure comprising:
   a head portion presenting a surface,
   a rear portion, and
   a deformable portion extending along a main axis connecting the head portion and the rear portion, the deformable portion being deformable in elongation/contraction along the main axis
   wherein the head portion comprises, at its surface, at least one propulsion cilium, one end of the at least one propulsion cilium being attached to the head portion and the other end of the at least one propulsion cilium being a free end configured to move freely in the viscous material,
   wherein the propulsion structure further comprises an actuator configured to actuate sequentially elongation/contraction cycles of the deformable portion,
   wherein the at least one propulsion cilium comprises a cilium body having an asymmetric cross section taken transversely to a longitudinal axis of the cilium body, and wherein the at least one propulsion cilium comprises a cilium body and an enlarged end portion forming the free end of the at least one propulsion cilium, wherein a cross-sectional area, at the enlarged end portion that taken transversely to a longitudinal axis of the cilium body is less than a cross-sectional area of the enlarged end portion in at least one plane parallel to the longitudinal axis of the cilium body.

2. The microrobot according to claim 1, wherein, for each elongation/contraction cycle of the deformable portion actuated by the actuator, the path of the free end of the at least one propulsion cilium in the viscous material in the contraction phase of the deformable portion is different from the path of the free end of the at least one propulsion cilium in the viscous material in the elongation phase of the deformable portion.

3. The microrobot according to claim 1, wherein the deformable portion comprises a bellows member having a front end attached to the head portion and a rear end attached to the rear portion.

4. The microrobot according to claim 3, wherein the peripheral wall of the bellows member presents peak portions and valley portions, two successive peak and valley portions being separated by a junction portion, and wherein a ratio of the thickness of the peak and valley portions to the thickness of the junction portions between two successive peak and valley portions is higher than 2.

5. The microrobot according to claim 1, wherein the rear portion comprises at its surface at least one propulsion cilium similar to, or different from, the at least one propulsion cilium of the head portion.

6. The microrobot according to claim 1, wherein the deformable portion comprises a spring member having a front end attached to the head portion and a rear end attached to the rear portion.

7. The microrobot according to claim 1, comprising at least two propulsion structures positioned in a row, wherein the actuators of the propulsion structures are configured to actuate elongation/contraction cycles of the deformable portions of the propulsion structures in predefined sequences so as to generate a non-reciprocal motion of the microrobot in the viscous material.

8. The microrobot according to claim 1, wherein the actuator comprises a piezoelectric transducer.

9. The microrobot according to claim 1, wherein the actuator comprises a pump, in particular an electroosmotic pump.

10. The microrobot according to claim 1, wherein the actuator comprises an electromagnetic transducer including a combination of an electromagnetic coil attached at one end of the deformable portion and a magnet attached at the other end of the deformable portion.

11. The microrobot according to claim 1, wherein the deformable portion is made of a polymer having a Young's modulus between 0.1 and 10 GPa, preferably between 0.5 and 2 GPa.

12. The microrobot according to claim 1, wherein the at least one propulsion cilium is made of the same material as the deformable portion.

13. The microrobot according to claim 1, wherein the microrobot is configured to move in a fluidic material at low Reynolds number, with a Reynolds number Re between $10^{-5}$ and $10^{-1}$.

* * * * *